United States Patent [19]
Williams

[11] Patent Number: 5,573,015
[45] Date of Patent: Nov. 12, 1996

[54] EXTRUDED EAR PLUG

[76] Inventor: Colin D. Williams, 9218 Hampton Oaks La., Charlotte, N.C. 28270

[21] Appl. No.: 412,283

[22] Filed: Mar. 28, 1995

[51] Int. Cl.⁶ .................................................. A61F 11/00
[52] U.S. Cl. ................................. 128/864; 128/865
[58] Field of Search ............................... 128/858–864; 264/222, 466

[56] References Cited

U.S. PATENT DOCUMENTS

| | | | |
|---|---|---|---|
| 2,538,339 | 1/1951 | Thomas | 128/864 |
| 2,785,675 | 3/1957 | Berkman . | |
| 3,565,069 | 2/1971 | Miller . | |
| 3,736,929 | 6/1973 | Mills | 128/864 |
| 3,872,559 | 3/1975 | Leight . | |
| 4,158,087 | 6/1979 | Wood . | |
| 4,219,018 | 8/1980 | Draper | 128/864 |
| 4,434,794 | 3/1984 | Leight . | |
| 4,498,469 | 2/1985 | Csiki . | |
| 4,552,137 | 11/1985 | Strauss . | |
| 4,582,053 | 4/1986 | Wilson . | |
| 4,702,238 | 10/1987 | Scott . | |
| 4,774,938 | 10/1988 | Leight . | |
| 5,008,058 | 4/1991 | Henneberger et al. . | |
| 5,044,463 | 9/1991 | Carr . | |
| 5,074,375 | 12/1991 | Grozil | 128/864 |
| 5,080,110 | 1/1992 | Weldon et al. . | |
| 5,131,411 | 7/1992 | Casali | 128/864 |
| 5,188,123 | 2/1993 | Gardner, Jr. . | |

*Primary Examiner*—Michael A. Brown
*Attorney, Agent, or Firm*—Bell, Seltzer, Park & Gibson, P.A.

[57] ABSTRACT

An earplug having a compressible or deformable sheath component and a more rigid core component. The components are both extruded in order that they may be rapidly and efficiently produced, and then the extrudate is cut into discrete pieces to form earplugs. The earplugs may be cut to form a variety of specially shaped end portions.

24 Claims, 2 Drawing Sheets

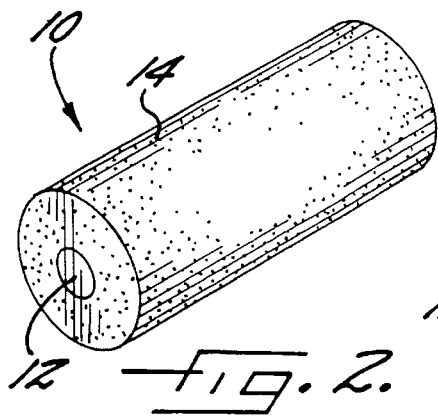
fig. 2.
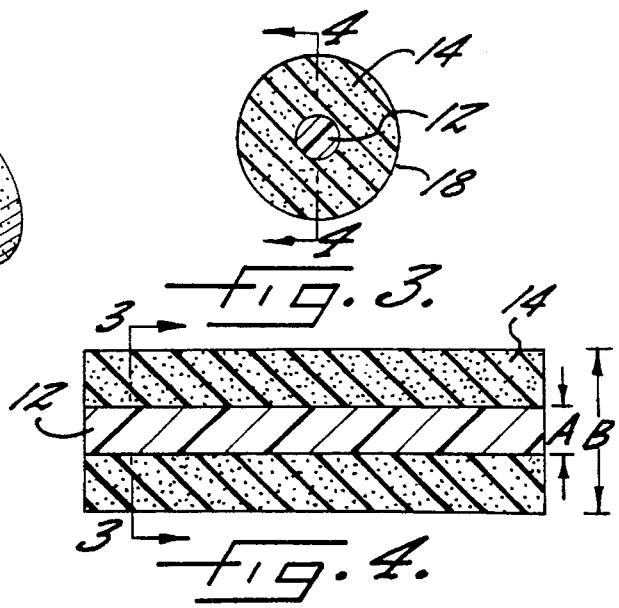
fig. 3.
fig. 4.
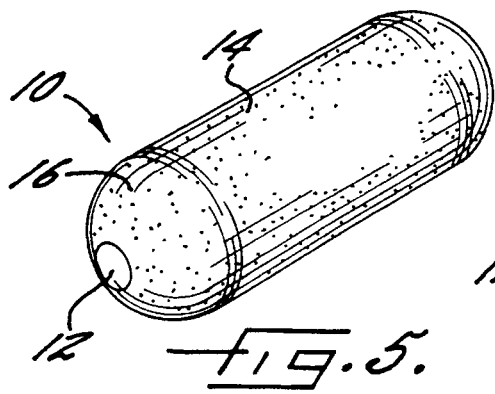
fig. 5.
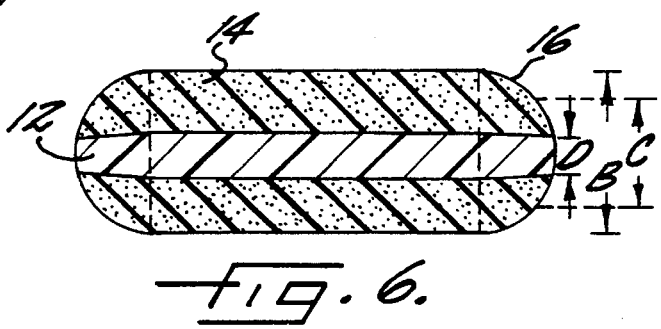
fig. 6.
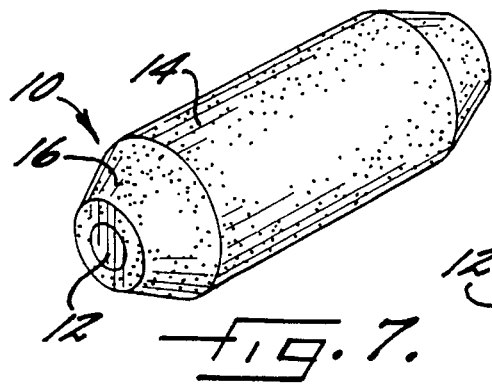
fig. 7.
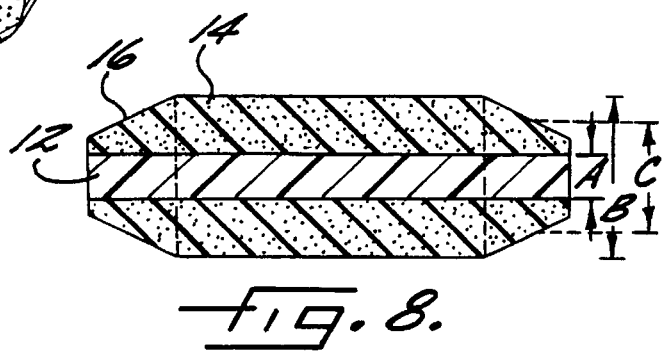
fig. 8.

EXTRUDED EAR PLUG

FIELD OF THE INVENTION

The present invention relates to multi-component extruded earplugs for dampening airborne sound, and a method for producing such earplugs.

BACKGROUND OF THE INVENTION

Earplugs designed to be inserted into a person's ear canals to dampen sound and prevent the entry of foreign matter are known in the art. Historically, these earplugs were manufactured from fibrous materials such as cotton. In more recent times, earplugs have been produced from polymer based materials, which tend to be more durable than the fibrous materials formerly used. One conventional method for making polymer-based earplugs is by die cutting plugs from sheets of cellular material such as vinyl or polyurethane foam. Such die cut plugs are usually cylindrically shaped in order that the earplugs can readily conform to the shape of a human ear canal. As a result, the amount of material waste in die cut plug production tends to be great because the web between cut cylindrical earplugs cannot be used. Because the material used is often not recyclable, disposal of the waste material can represent a significant manufacturing expense. In addition, earplugs produced by this method customarily have cut cells along their cylindrical surfaces. As a result, they have a rough surface which can be uncomfortable to the wearer and harbor dirt. These earplugs can also be difficult to insert into a wearer's ear canals because they tend to lack longitudinal rigidity.

Another method for producing polymer-based earplugs is by molding them to the desired shape. For example, U.S. Pat. Nos. 4,774,938 and 3,872,559, both to Leight, disclose earplugs molded from polymer-based materials. Molded earplugs can be manufactured so that they are specially shaped and covered by a protective skin, enhancing their comfort and fit. However, the process of molding earplugs tends to be slower and more capital intensive than die cutting due to the large number of molds required. In addition, molded earplugs are often difficult to insert into a user's ears due to the fact that the polymer materials from which they are manufactured tend to lack longitudinal rigidity.

Attempts have been made to provide earplugs having sufficient longitudinal rigidity to allow them to be easily inserted into the ears and sufficient compressibility to allow snug yet comfortable wearer fit. For example, multi-component earplugs having a compressible element and a more rigid element are taught by U.S. Pat. No. 5,188,123 to Gardner, Jr. and U.S. Pat. No. 4,434,794 to Leight. Because the rigid and compressible elements of those earplugs must be individually manufactured and then joined together, their production processes tend to be slower and more costly than those for die cut earplugs. Thus a need exists for a readily manufacturable and inexpensive sound dampening earplug providing the requisite stiffness for easy ear insertion along with comfortable fit.

SUMMARY AND OBJECTS OF THE INVENTION

It is therefore an object of the present invention to provide a multi-component earplug which can be readily inserted into the ear of a user.

It is also an object of the present invention to provide an earplug which can be readily and inexpensively manufactured.

Further, it is an object of the invention to provide a method for efficiently making such an earplug.

These and other objects are accomplished by providing an earplug having core and sheath components which are both extruded to form a composite structure and then cut to form individual earplugs. The core component may be extruded initially and then fed to a cross-head or other such type of extruder where it is covered with an outer sheath. Alternatively, the core and sheath components may be coextruded simultaneously to form the composite structure.

The core component may be somewhat flexible, but desirably is semi-rigid in order to provide structural support for the earplug. The core component can be made of a solid or cellular elastomeric material and may be compressible or deformable. In addition, the core component may have any of a variety of cross-sectional configurations such as circular, polygonal or irregular, and desirably has a diameter of between about 1 and 5 millimeters.

The outer sheath component is less rigid than the core component, and is preferably formed of a compressible or deformable elastomeric material in order that the earplug can be compressed and inserted into a wearer's ear. The sheath component surrounds the core component and preferably the components are bonded along their common surfaces by the cohesive forces acting between the respective elastomeric materials.

The sheath component may also include a continuous skin about its outer surface. This is particularly desirable where the sheath component is formed from a cellular-type material, as the continuous skin protects the cells from exposure and prevents them from harboring soil. The skin can be integrally formed during the extrusion of the sheath or produced by additional manufacturing steps.

The composite structure is then cut into discrete pieces about 10–35 millimeters in length to form individual earplugs. The composite structure may be cut at an angle approximately 90° to a longitudinal axis of the core component to form squared-off planar ends on the discrete pieces. Alternatively, the composite structure may be sculpture cut, where it is compressed in specific regions and cut while in the compressed condition to form earplugs having specially shaped end portions. In a preferred embodiment of the invention, the composite structure is fused while it is in a compressed condition to form earplugs having end portions with reduced diameters. These methods may be used to form earplugs having a variety of end portion configurations such as conically or hemispherically shaped. The special shaping of the end portions can enable the earplugs to better fit a user's ear canals, thereby enhancing the ability of the plug to block sound and increasing wearer comfort. The earplugs may have two similarly shaped end portions, or may have two ends of different constructions.

The composite structure forming the earplug is preferably capable of being compressed or deformed by hand down to about 40% of its original diameter. The composite structure desirably possesses a slow recovery from compression or deformation in order that an earplug can be pressed to a smaller diameter for ear insertion; the earplug then desirably proceeds returning to its original dimensions, thereby achieving a snug fit within the wearer's ear.

BRIEF DESCRIPTION OF THE DRAWINGS

FIG. 3 is a cross-sectional view of the earplug shown in FIGS. 2 and 4, as shown along line 3—3 of FIG. 4;

FIG. 4 is a longitudinal cross-sectional view taken along line 4—4 of FIG. 3;

FIG. 5 is a perspective view of an earplug of the present invention having hemispherically shaped end portions;

FIG. 6 is a longitudinal cross-sectional view of the earplug shown in FIG. 5;

FIG. 7 is a perspective view of an earplug according to the present invention having conically shaped end portions;

FIG. 8 is a longitudinal cross-sectional view of the earplug shown in FIG. 7; and FIG. 9 shows one preferred production method for the earplugs in accordance with the present invention.

DETAILED DESCRIPTION OF THE PREFERRED EMBODIMENT

Figure 1:
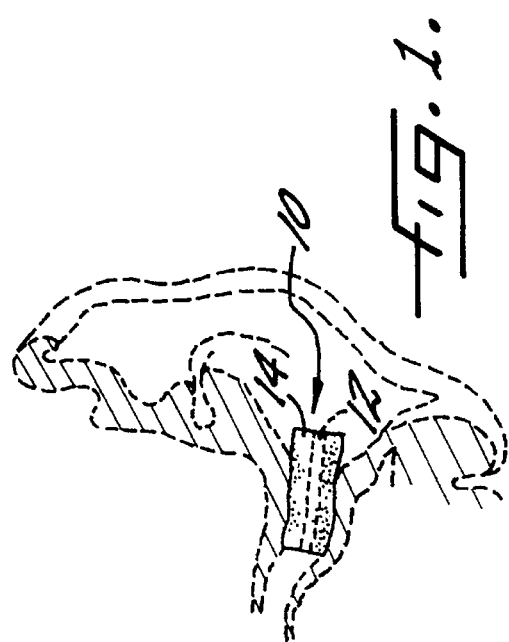
FIG. 1 is an environmental view of an earplug according to the present invention inserted in a wearer's ear.

Referring now to FIGS. 1–9, the present invention is directed to an earplug 10 designed to be inserted in a human ear canal for dampening airborne sound and protecting against the entry of foreign matter into the ear canal. The earplug 10 of the present invention comprises a composite structure including a core component 12 and a sheath component 14 covering the core component. The core component 12 is preferably stiffer than the sheath component 14 and preferably semi-rigid, in order that it can provide structural rigidity for the earplug. This structural rigidity allows the earplugs 10 to be more easily inserted into a wearer's ears. The sheath component 14 is preferably softer and more flexible than the core component 12 so that it provides a comfortable fit for the wearer. The earplug 10 is desirably compressible or deformable in order that it can be compressed and inserted into a wearer's ear canal.

The core component 12 is preferably extruded from an extrudable elastomeric material such as a thermoplastic elastomer material or a vulcanizable cross-linked or crosslinkable elastomer. The core component 12 can be of a solid material such as a viscoelastic polymer material, or a cellular material, provided that the core component provides structural rigidity for the composite structure. The material can also be compressible or deformable, provided the core component is able to provide the requisite rigidity to the composite structure. When the material is compressible or deformable, its rate of recovery from compression or deformation preferably is slow. Particularly preferred are materials having a rate of recovery from compression of between about 2 and 120 seconds.

Preferred materials for forming the core component are thermoplastic elastomers such as thermoplastic polyolefins/ethylene-propylene (YEPM), thermoplastic block copolymers/styrene-butadiene (YSBR) and styrene-isoprene (YSIR), thermoplastic polyester (Y), thermoplastic polyurethane/polyester (YAU)/polyether (YEA), thermoplastic vulcanizates, melt processible rubbers, polyamide blocks, thermoplastic rubber, and viscoelastic polyurethane. Particularly preferred are thermoplastic elastomers sold by DSM Thermoplastic Elastomers Inc. under the name SARLINK, Chemigum®P83/PVC thermoplastic elastomers sold by Goodyear Chemicals, and Santoprene® thermoplastic rubber sold by Monsanto. When the core is made from a solid material, its specific gravity is desirably between about 0.9 and 1.4, and preferably between about 1 and 1.1. When the core is made from a cellular material, its specific gravity is desirably less than 1, and preferably between about 0.2 and 0.8. When the core component 12 is formed from a cellular material, the cells may be formed by mechanical incorporation of gases such as air, nitrogen or carbon dioxide into the base polymer. Alternatively, a chemical blowing agent can be incorporated into the base polymer. The blowing agent is then activated, usually by heat, to form a cellular polymer material. The cellular material formed can in either case be closed or open celled.

As shown in FIGS. 1–8, the core component 12 preferably has a circular cross-section, though other cross-sectional shapes can be used. For example, the cross-section of the core component could be polygonally or irregularly shaped. The diameter A of the core component 12 is ideally between about 0.5 mm and 5 mm and preferably about 2.5 mm.

The sheath component 14 preferably completely surrounds the core component 12 so as to be bonded thereto. The bonding is preferably continuous along the common surfaces of the components. In addition, the sheath component 14 desirably has a consistent cross-sectional diameter B. The sheath component 14 is less rigid than the core component 12 and preferably softer than the core component so that it is comfortable to a wearer. The sheath component 14 is preferably made from a compressible or deformable material such as a thermoplastic elastomer of a crosslinked or crosslinkable polymer or a viscoelastic polymer material. The material desirably has a slow recovery from compression or deformation. Particularly preferred are materials having a rate of recovery from compression of between about 2 and 120 seconds. The material can be a solid or a cellular material.

Preferred materials for forming the sheath component 14 are thermoplastic elastomers such as thermoplastic Polyolefins/ethylene-propylene (YEPM), thermoplastic block copolymers/styrene-butadiene (YSBR) and styrene-isoprene (YSIR), thermoplastic polyester (Y), thermoplastic polyurethane/polyester (YAU)/polyether (YEA), thermoplastic vulcanizates, melt processible rubbers, polyamide blocks, thermoplastic rubber, and viscoelastic polyurethane. Particularly preferred are thermoplastic elastomers sold by DSM Thermoplastic Elastomers Inc. under the name SARLINK, Chemigum®P83/PVC thermoplastic elastomers sold by Goodyear Chemicals, and Santoprene® thermoplastic rubber sold by Monsanto. The sheath material desirably has a specific gravity of between about 0.2 and 0.5. When the sheath component 14 is formed from a cellular material, the cells may be formed either by mechanical incorporation of gases such as air, nitrogen or carbon dioxide into the base polymer, or by the incorporation of a chemical blowing agent into the base polymer. The blowing agent is then activated, usually by heat, to form a cellular polymer material. The material may in either case be an open or closed cell material.

The core component 12 and the sheath component 14 are desirably made from the same base polymer, with the sheath and core components being made from different formulations of the polymer or being treated so that the core component 12 is more rigid than the sheath component 14. For example, the same base polymer could be used to form the core and sheath components 12 and 14, with more plasticizer being included in the material which is to form the sheath component 14 in order that it is less rigid than the core component 14. In this way, it can be ensured that the core and sheath components 12 and 14 are compatible, and the sheath component 14 tends to adhere particularly well to the core component 12 due to the cohesive bonding which occurs between the materials of the two components. In addition, using two materials from the same base polymer can result in manufacturing efficiencies, which will be discussed more fully below with respect to the method.

Alternatively, the core and sheath components 12 and 14 can be made from different materials, provided they are sufficiently compatible to form the desired composite structure. For example, both of the components could be formed from a compressible or deformable material or only one of the components could be compressible or deformable. Alternatively, one or both of the components could be formed from a cellular material or solid material. In order that the earplug 10 can conform to the shape of a wearer's ear canal, it is preferable that the combination of component materials provides a composite structure that is compressible by hand to down to 40% of its original diameter.

The cross-sectional shape of the sheath component 14 is preferably circular (as shown in FIGS. 1–8) though it can also be otherwise shaped, such as polygonal or irregular shaped. The preferred cross-sectional diameter B of the sheath component is between about 5 mm and 20 mm, preferably about 10–15 mm.

In a preferred embodiment of the invention, the sheath component 14 includes a continuous skin 18 about its outer surface. This is particularly desirable where the sheath component 14 is formed from a cellular material because the continuous skin 18 protects any open cells along the outer surface from harboring soil. The continuous skin 18 is preferably integrally formed as a result of the extrusion process. However, it can also be provided through chemical or mechanical treatment of the composite structure or it can be provided as an additional layer.

Figure 2:
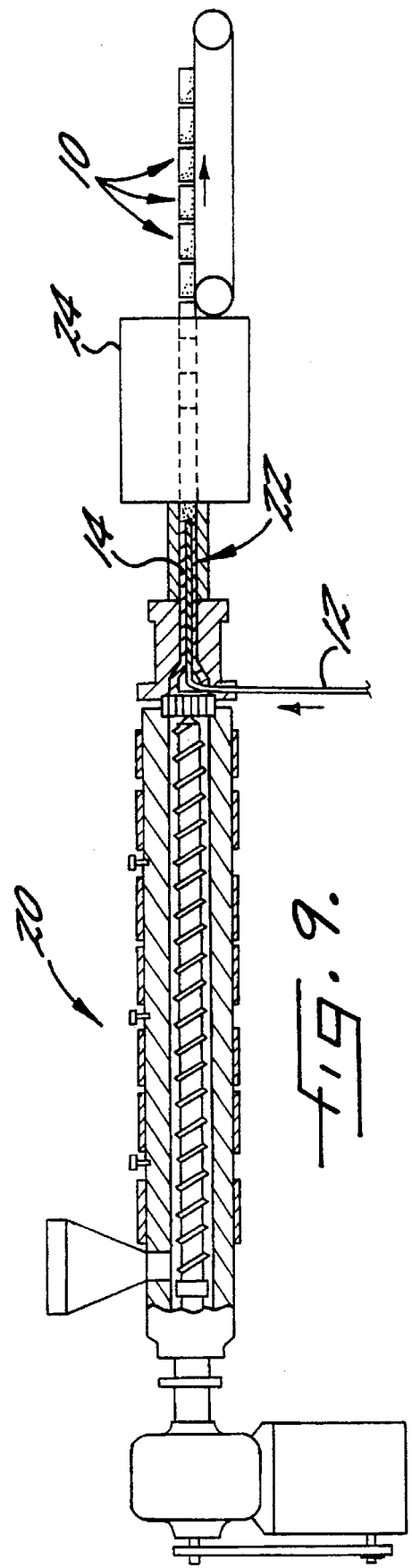
FIG. 2 is a perspective view of an earplug according to the present invention having squared-off, planar end portions.

As shown in FIGS. 2 and 4–8, the end portions 16 of the earplugs 10 may have any of a variety of configurations. Particularly desirable are earplugs having end portions 16 which have a smaller diameter (C) than the diameter (B) of the sheath component forming the rest of the earplug 10, as shown in FIGS. 6 and 7. For example, the earplugs may have hemispherically or conically shaped end portions 16, as shown in FIGS. 5 and 7, respectively. The smaller diametered or tapered end portions 16 of the earplugs 16 allow them to be readily inserted into a wearer's ear canals. When the earplug has end portions having a reduced diameter (C), as shown, for example, in FIGS. 6 and 8, the core component 12 can also have a reduced diameter (D), as shown in FIG. 6. Alternatively, the diameter of the core component 12 can have a constant diameter (A), though the diameter (C) of the end portions is smaller than the diameter (B) of the sheath component forming the rest of the earplug. Alternatively, the earplugs 10 can have squared-off planar end portions and a consistent diameter throughout the earplug length, as shown in FIGS. 2 and 4.

The earplugs desirably include two end portions 16 which are of the same shape. However, combinations can be used such as a conical end portion on one end of the earplug and a hemispherical end portion on the other end of the earplug so that the wearer may select which shaped end portion is more comfortable in his ear and insert that shaped end portion into his ear. Also, in the illustrated embodiments, the components 12 and 14 are coextensive in length, and the core component 14 is exposed at each end of the earplug.

The manufacture of the earplugs may be performed as shown in FIG. 9. An elastomeric material is extruded to form a long rod-like element which forms the core component 12. This core component 12 is then fed into the outlet head of a conventional extruder 20, and the sheath component 14 is extruded about the core component to form a composite structure 22. Crosshead or other types of extruders conventionally used for biaxial or uniaxial extrusions, such as those used in the manufacture of plastic and rubber coated wires and hoses, can be used to form the coaxial components. Particularly preferred are extruders which utilize a cavity transfer mixer between the extruder barrel and the die such as the CTM® cavity transfer mixer distributed by RAPRA Technology Limited of the United Kingdom. Alternatively, the core component 12 and sheath component 14 can be coextruded simultaneously by a single extruder using conventional simultaneous coextrusion methods.

The composite structure extrudate 22 is then solidified, with the solidification means being dependent on the material used to form the extrudate. For example, composite structure extrudates formed from thermoplastic materials can be quenched by way of traditional cooling methods, such as treating with a liquid or gas bath to cool and solidify the extrudate. Particularly preferred for the quench bath is temperature controlled air, as this represents a particularly cost effective and available bath medium. In the case of non-thermoplastic elastomer composite structure materials, the extrudate can be crosslinked, if necessary, and vulcanized.

It is particularly preferred to form the core and sheath components from the same base polymer in order that the components readily bond together. The co-extrusion process as described herein results in the core component and the sheath component being bonded together at their interface by cohesive forces, which may be defined as the forces resulting from the tendency of components of like composition to hold together as a result of intermolecular attraction. Thus a separate adhesive is not required.

After the composite structure 22 has cooled, it is then fed to a cutting device 24 which cuts the composite structure into discrete pieces of the desired length, preferably about 10 to 35 mm, thereby forming individual earplugs. Particularly preferred are earplugs having a length of about 17 to 25 mm. The composite structure may be cut into discrete pieces using any of a variety of conventional cutting devices such as a knife blade, hot wire, water jet, or laser, for example. A particularly preferred machine for cutting the composite structure into earplugs is the high speed wire and tubing cutter Model WC500 sold by the Eraser Company Inc.

In a preferred method of the invention, the composite structure can be cut to form discrete pieces using a cutting device similar to the iris shutter assembly used in photographic cameras. This type of cutting device can be used to radially compress the composite structure while cutting it. When it is desired to form earplugs having end portions with reduced or shaped diameters, a composite structure made from a thermoplastic material can be fed to a heated device which compresses and cuts the composite structure. Because the composite structure is heated while it is radially compressed, it retains its compressed configuration following cutting, resulting in end portions of reduced diameter. Compression can be effected to produce end portions having specific configurations, such as conical or hemispherical. The heat can be provided by either directly heating the iris blades or by applying local heat to the tip of the compressed core by a laser or other localized heating device. Alternatively, the compression may be performed prior to complete solidification of the composite structure or while the material of the composite structure, and particularly that of the sheath component 14, is still in its semifluid state, to thereby form end portions having reduced diameters.

In a further alternative method, the composite structure can be compressed in specific regions and cut (in a manner similar to that used to produce sculpted foam pillows) to form sculpted earplug end portions.

It is noted that the above-noted production methods generate little, if any, material waste. However, the earplugs can be made from materials which are readily recyclable. When the core and sheath components 12 and 14 are made from the same base polymer, any waste material which may result from the manufacturing process can be returned to the material supply for the next earplug production batch.

The completed earplugs are desirably provided and packaged in pairs. However, due to the inexpensive and rapid production method taught by the present invention, the earplugs may be provided at a cost sufficiently low for them to be used in a disposable manner whereby they are discarded after a single wearing. However, the resulting earplugs are durable enough that they will withstand repeated wearings by the user.

That which is claimed is:

1. A method of making an earplug comprising the steps of:
    extruding a core component about 1–5 millimeters in diameter from an extrudable elastomeric material,
    extruding an outer layer of an extrudable elastomeric material, which is compressible and less rigid when solidified than the material of the core component, over said core component to form a composite structure having a diameter of about 5–20 millimeters, and
    cutting the composite structure into discrete pieces about 10–35 millimeters in length, thereby forming individual earplugs.

2. The method of claim 1, wherein said steps of extruding a core component and extruding an outer layer over the core component are performed simultaneously.

3. The method of claim 1, wherein said step of cutting the composite structure comprises cutting the composite structure at a 90° angle to a longitudinal axis of the core component, thereby forming substantially planar ends on said discrete pieces.

4. The method of claim 1, further comprising the step of forming a protective skin over the composite structure.

5. The method of claim 1, further comprising the step of radially compressing the composite structure while cutting it.

6. The method of claim 5, further comprising the step of fusing the composite structure while it is being radially compressed to form discrete pieces having end portions with smaller diameters than the diameter of the composite structure.

7. The method of claim 6, wherein said steps of compressing and fusing are performed to form discrete pieces having conical end portions.

8. The method of claim 6, wherein said steps of compressing and fusing are performed to form discrete pieces having hemispherically-shaped end portions.

9. The method of claim 1, wherein said step of extruding an outer layer of a compressible extrudable material comprises extruding a material having a specific gravity of between about 0.2 and 0.5 and a rate of recovery from compression of between about 2 and 20 seconds.

10. A multi-component earplug formed by the method of claim 1.

11. An earplug sized for being received in the human ear canal and comprising a rod-shaped core component composed of a relatively rigid elastomeric material, a sheath component coaxially surrounding said core component and being composed of a relatively non-rigid and soft elastomeric material, and with the core component and the sheath component being bonded together along the entire length of said core component by cohesive forces between the respective elastomeric materials.

12. The earplug as defined in claim 11 wherein said sheath component comprises a foamed thermoplastic elastomer.

13. The earplug as defined in claim 12 wherein said sheath component has a continuous outer skin.

14. The earplug as defined in claim 13 wherein the elastomeric materials of the core component and the sheath component consist essentially of the same thermoplastic elastomer.

15. The earplug as defined in claim 11 wherein said core component and said sheath component are coextensive in length such that the core component is exposed at each end of the earplug.

16. The earplug as defined in claim 15 wherein said sheath component has a generally cylindrical outer surface along at least the majority of its length.

17. The earplug as defined in claim 16 wherein said sheath component has an outer diameter which is at least about three times the diameter of said core component.

18. A multi-component earplug comprising a composite structure including a core component of an elastomeric material substantially enclosed by a sheath component of an elastomeric material such that an inner surface of said sheath component extends continuously about an outer surface of said core component and is bonded thereto, said core component being more rigid than said sheath component, and said composite structure having first and second end portions defining a composite structure length therebetween of about 10 to 35 millimeters, said core component having a cross-sectional diameter of about 1 to 5 millimeters and said composite structure having a cross-sectional diameter of about 5 to 20 millimeters, thereby enabling it to snugly fit within an ear canal of a user.

19. The multi-component earplug of claim 18, wherein said composite structure has a substantially consistent cross-sectional diameter throughout its length.

20. The multi-component earplug of claim 18, wherein the composite structure has a smaller cross-sectional diameter about the first and second end portions than about the rest of the composite structure length.

21. The multi-component earplug of claim 18, wherein said core component is made from a material having a specific gravity of between about 0.2 and 1.4 and said sheath component has a specific gravity of between about 0.2 and 0.5.

22. The multi-component earplug of claim 18, wherein said sheath component is formed of a cellular elastomeric material.

23. The multi-component earplug of claim 18, further comprising a continuous skin about the outer surface of said composite structure.

24. The multi-component earplug of claim 18, wherein said composite structure has a rate of recovery from compression of between about 2 and 120 seconds.

* * * * *